(12) United States Patent
Maida et al.

(10) Patent No.: US 7,308,129 B2
(45) Date of Patent: Dec. 11, 2007

(54) CHARACTERISTIC AMOUNT CALCULATING DEVICE FOR SOLDERING INSPECTION

(75) Inventors: Masatomo Maida, Kawasaki (JP); Shuzo Igarashi, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 830 days.

(21) Appl. No.: 10/691,556

(22) Filed: Oct. 24, 2003

(65) Prior Publication Data
US 2004/0101190 A1  May 27, 2004

(30) Foreign Application Priority Data
Nov. 21, 2002  (JP)  .............. 2002-338141

(51) Int. Cl.
*G06K 9/00* (2006.01)
(52) U.S. Cl. .................................. 382/150; 228/180.1
(58) Field of Classification Search .............. 228/56.3, 228/111.5, 180.1, 262.31, 262.42, 262.45, 228/262.51, 262.61, 262.72, 262.8, 262.9; 382/150
See application file for complete search history.

(56) References Cited

U.S. PATENT DOCUMENTS

| | | | | |
|---|---|---|---|---|
| 3,665,367 A | * | 5/1972 | Keller et al. ............... | 439/866 |
| 4,876,455 A | * | 10/1989 | Sanderson et al. ..... | 250/559.22 |
| 5,064,291 A | * | 11/1991 | Reiser ....................... | 356/625 |
| 5,164,994 A | * | 11/1992 | Bushroe ..................... | 382/150 |
| 6,249,598 B1 | * | 6/2001 | Honda et al. ............... | 382/150 |
| 2003/0021718 A1 | * | 1/2003 | Munekata et al. .......... | 420/560 |

FOREIGN PATENT DOCUMENTS

| | | |
|---|---|---|
| JP | 04-169803 | 6/1992 |
| JP | 05-035850 | 2/1993 |
| JP | 07-071932 | 3/1995 |
| JP | 10-141929 | 5/1998 |

\* cited by examiner

*Primary Examiner*—Matthew C. Bella
*Assistant Examiner*—G. F. Cunningham
(74) *Attorney, Agent, or Firm*—Staas & Halsey LLP

(57) ABSTRACT

A characteristic amount calculating device for soldering inspection. The characteristic amount calculating device includes a design information inputting section for inputting design information of an inspection object, an inspection standard inputting section for inputting an inspection standard, a solder shape calculating section for calculating shape information of a solder fillet according to the design information, and an inspection image calculating section for calculating an inspection image according to the shape information. The characteristic amount calculating device further includes a characteristic amount calculating section for calculating a characteristic amount from the inspection image, a solder shape defective/nondefective determinating section for determining whether the solder shape is defective or nondefective from the shape information by using the inspection standard, and a characteristic amount outputting section for displaying or outputting the characteristic amount and a result of defective/nondefective determination.

12 Claims, 18 Drawing Sheets

FILLET CURVE : $F_1(u)$

COMPONENT WET CONDITION CURVE : $F_2(u)$

LAND WET CONDITION CURVE : $F_3(u)$

FIG. 10
SOLDER SHAPE TABLE
| LONGITUDINAL DEVIATION | LATERAL DEVIATION | BASIC SHAPE | WICKING RATE | SPREADING RATE | SOLDER AMOUNT | SOLDER SHAPE |
|---|---|---|---|---|---|---|
| 0 | 0 | 1-1-1 | 100% | 100% | 1416 |  |
| 0 | 0 | 2-1-1 | 100% | 100% | 1658 |  |
| 0 | 0 | 3-1-1 | 100% | 100% | 2883 |  |
| 0 | 0 | 4-1-1 | 40% | 100% | 1460 |  |
| -5 | 0 | 2-1-1 | 100% | 100% | 1410 |  |
| 0 | 0 | 5-1-1 | 100% | 100% | 397 |  |

FIG. 20
| INSPECTION IMAGE TABLE | CHARACTERISTIC AMOUNT TABLE | | | DEFECTIVE/NONDEFECTIVE DETERMINATION TABLE | | |
|---|---|---|---|---|---|---|
| INSPECTION IMAGE | MEASURED VALUE 1 | ... | MEASURED VALUE n | SHORT SOLDER | EXCESS SOLDER | WETTABILITY |
|  | 91 | ... | 60 | ○ | ○ | ○ |
|  | 44 | ... | 13 | ○ | ○ | ○ |
|  | 9 | ... | 0 | ○ | POOR | ○ |
|  | 59 | ... | 13 | ○ | ○ | POOR |
|  | 50 | ... | 32 | ○ | ○ | ○ |
|  | 100 | ... | 0 | POOR | ○ | ○ |
|  |  |  |  |  |  |  |

CHARACTERISTIC AMOUNT CALCULATING DEVICE FOR SOLDERING INSPECTION

BACKGROUND OF THE INVENTION

1. Field of the Invention

The present invention relates to a characteristic amount calculating device for soldering inspection for calculating a characteristic amount for use in generation of inspection data to be used in an optical or X-ray transmissive appearance inspecting machine for inspecting a soldered portion of a component mounted on a printed wiring board.

2. Description of the Related Art

The inspection of a soldered portion by the optical or X-ray transmissive appearance inspecting machine is performed by inspecting the shape of a solder bonding a land on a printed wiring board and a component to be mounted on the printed wiring board to thereby inspect the connected condition of the solder for the purpose of ensuring long-term reliability. Both in the optical appearance inspecting machine and in the X-ray transmissive appearance inspecting machine, an inspection image indicating the characteristic of the three-dimensional solder shape is picked up.

In the case of the optical appearance inspecting machine, light is directed onto the solder from the upper side of the printed wiring board and reflected light from the surface of the solder is picked up. The solder surface has a capability of specular reflection, so that light incident on the solder surface in a specific direction is reflected on the solder surface in a specific direction. Accordingly, the inspection image indicates the surface angle of the solder shape. In the case of the X-ray transmissive appearance inspecting machine, X rays are directed to the solder from the upper or lower side of the printed wiring board to pick up (intensity detect) transmitted X rays. The transmittance of the X rays continuously changes with the thickness of the solder, so that the inspection image indicates the thickness of the solder.

In general, the inspection image indicating the characteristic of the three-dimensional solder shape reflects a difference in solder shape between a defective and a nondefective, and therefore has different characteristics between the defective and the nondefective. Accordingly, the inspection is performed by measuring different characteristic amounts between the defective and the nondefective and providing a threshold therebetween to perform defective/nondefective determination. The characteristic amount means an intensity average in an arbitrary region of the inspection image or the length or area of a region having an arbitrary intensity. There is a large difference in characteristic amount between the defective and the nondefective in terms of a general solder shape. Accordingly, by setting the threshold between the characteristic amount of the defective and the characteristic amount of the nondefective, the inspection can be performed. However, there are variations in solder shape generated, so that the characteristic amount of the defective may be similar to the characteristic amount of the nondefective in some case.

In this case, there is a possibility of "overtight" determination such that an actual nondefective solder shape is erroneously determined as defective or "undertight" determination such that an actual defective solder shape is erroneously determined as nondefective, depending upon the threshold set above. The "overtight" determination causes an increase in number of times of visual inspection to be performed in the subsequent step, and the "undertight" determination further causes a reduction in nonadjusted ratio in the subsequent step, causing an increase in cost of the subsequent step. It is therefore desirable to minimize the "overtight" determination and the "undertight" determination by adjustment of the threshold or adjustment of inspection data including modification of an inspection region or modification of an inspection method.

The adjustment of inspection data must be performed as checking the circumstances of occurrence of the "undertight" or "overtight" determination for all the defective and nondefective solder shapes, because there is a case that an excess reduction in the "undertight" determination may cause an increase in the "overtight" determination, or there is a case that an excess reduction in the "overtight" determination may cause an increase in the "undertight" determination. Conventionally, the adjustment of inspection data is performed as checking the circumstances of occurrence of the "undertight" or "overtight" determination for solder shapes formed in the past, by collecting past characteristic amounts, inspection images, and results of defective/nondefective determination in visual inspection. In this case, the information on the characteristic amounts collected over a long period of time includes information on every solder shape, so that the adjustment of optimum inspection data can be performed.

However, the conventional method has three problems. The first problem is that long-term data collection related to solder shapes must be carried out. In the conventional method, the information on every solder shape is obtained by data collection. However, since the frequency of occurrence of solder shapes causing the "undertight" or "overtight" determination is low and these solder shapes are various, the data collection must be made for a long period of time, resulting in the requirement of much time for optimization of the inspection data.

The second problem is that the defective/nondefective determination is ambiguous. The "overtight" or "undertight" determination is made by the comparison of the determination result by the visual inspection in the subsequent step and the determination result by the appearance inspecting machine. That is, the determination result by the appearance inspecting machine is evaluated under the condition that the determination result by the visual inspection is correct. However, the visual inspection is made by human sensory inspection with reference to an inspection standard on a solder amount and solder wettability. As a result, the defective/nondefective determination in the visual inspection is ambiguous, causing an interference with the optimization of inspection data. For example, there is a case that an actual defective may be determined as a nondefective in the visual inspection, causing the occurrence of false "overtight" determination. When data adjustment is made against this occurrence, "undertight" determination actually occurs rather than reducing the "overtight" determination.

The third problem is that there are variations in inspection image due to any factors other than solder shapes. The adjustment of inspection data should be made for a solder shape determining a defective or a nondefective. However, an inspection image and a characteristic amount are not in one-to-one correspondence to a solder shape, but vary due to any factors such as a solder surface condition other than solder shapes. As a result, there is a case that an extremely rare inspection image may be produced outside the range of normal variations due to solder shapes. If the inspection data is adjusted for such a rare inspection image, there is a possibility that the "undertight" or "overtight" determination may increase. Therefore, such a rare inspection image must be removed from the object to data adjustment. However, it is difficult to distinguish between such a rare inspection image and a normal inspection image, thus causing a difficulty of optimization of inspection data.

SUMMARY OF THE INVENTION

It is therefore an object of the present invention to provide a characteristic amount calculating device for soldering inspection which can obtain a characteristic amount in a short period of time.

It is another object of the present invention to provide a characteristic amount calculating device for soldering inspection which can obtain a characteristic amount in a short period of time and can perform a precise defective/nondefective determination.

In accordance with an aspect of the present invention, there is provided a characteristic amount calculating device for soldering inspection, including design information inputting means for inputting design information of an inspection object; inspection standard inputting means for inputting an inspection standard; solder shape calculating means for calculating shape information of a solder fillet according to the design information; inspection image calculating means for calculating an inspection image according to the shape information of the solder fillet; characteristic amount calculating means for calculating a characteristic amount from the inspection image; solder shape defective/nondefective determining means for determining whether the solder shape is defective or nondefective from the shape information by using the inspection standard; and characteristic amount outputting means for displaying or outputting the characteristic amount and a result of defective/nondefective determination.

The design information includes a component shape and a land shape, and the solder shape calculating means calculates a plurality of solder shape data according to the component shape and the land shape input. Preferably, the design information includes a component mounting position, a solder wicking position, a solder spreading position, and a solder basic shape independent of design/manufacture conditions. The solder shape calculating means calculates a plurality of solder shape data according to the component mounting position, the solder wicking position, the solder spreading position, and the solder basic shape input.

The solder shape calculating means calculates three-dimensional coordinate data by using a fillet curve showing the contour of the solder fillet, a wicking curve showing a solder wicking condition on a component surface, and a spreading curve showing a solder spreading condition on a land surface. The inspection image calculating means has inspection image obtaining means for obtaining the inspection image by using an inspection image obtaining function indicating the intensity of the inspection image with respect to the characteristic amount including the angle or thickness of the solder fillet.

The inspection image obtaining function is calculated by using an actual inspection image of a solder fillet formed on a land at an unmounted portion as a function showing the intensity of the inspection image with respect to the characteristic amount including the angle or thickness of the solder fillet. Preferably, the inspection standard includes a solder amount standard, a solder wicking standard, and a solder spreading standard. The solder shape defective/nondefective determining means performs the defective/nondefective determination for a virtual solder shape by using the inspection standard specifying a defective range on a solder amount or a solder wetting amount.

The characteristic amount outputting means outputs information selected from the group consisting of a solder shape, solder amount, wetting amount, and inspection image shown by three-dimensional coordinate data, in addition to the characteristic amount and the defective/nondefective determination result. Preferably, the characteristic amount outputting means specifies a threshold related to the characteristic amount to thereby display a solder shape determined as undertight or overtight.

The above and other objects, features and advantages of the present invention and the manner of realizing them will become more apparent, and the invention itself will best be understood from a study of the following description and appended claims with reference to the attached drawings showing some preferred embodiments of the invention.

BRIEF DESCRIPTION OF THE DRAWINGS

FIG. 10 is an output example of the solder shape table;

FIG. 20 is an output example of an inspection image table, characteristic amount table, and defective/nondefective determination table.

DETAILED DESCRIPTION OF THE PREFERRED EMBODIMENTS

Figure 1:
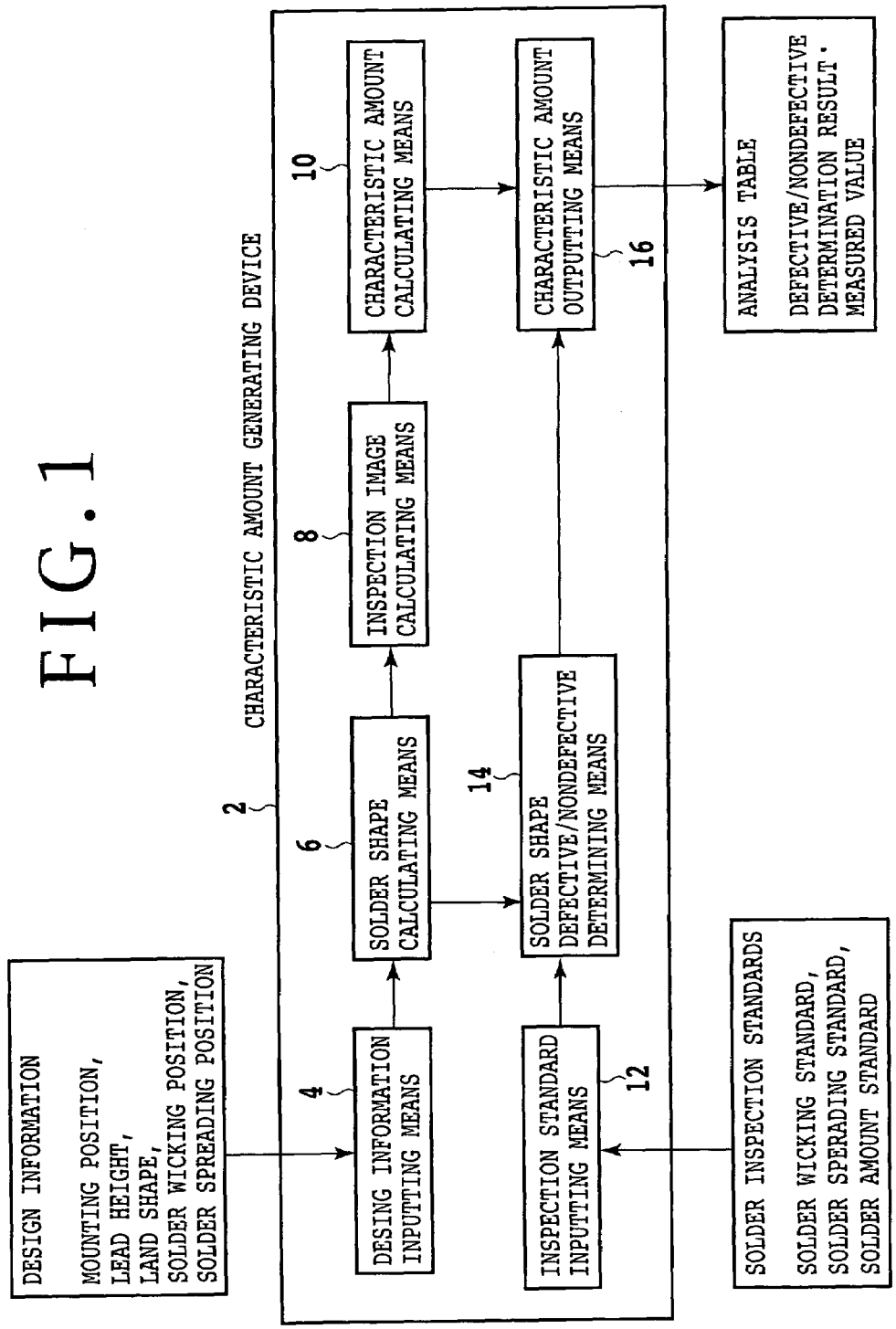
FIG. 1 is a block diagram of a characteristic amount generating device according to the present invention.

A preferred embodiment of the present invention will now be described in detail with reference to the drawings. FIG. 1 is a block diagram of a characteristic amount generating device 2 according to a preferred embodiment of the present invention. The characteristic amount generating device 2 includes design information inputting means 4 for inputting design information, solder shape calculating means 6 for outputting a plurality of three-dimensional solder shape data according to the design information, and inspection image calculating means 8 for outputting an inspection image according to an inspecting machine (optical appearance inspecting machine or X-ray transmissive appearance inspecting machine) using the above three-dimensional solder shape data.

The characteristic amount generating device 2 further includes characteristic amount calculating means 10 for calculating a characteristic amount for the inspection image according to a characteristic amount specifying method in each inspecting machine, inspection standard inputting means 12 for inputting inspection standards such as a solder amount and a wetting amount as the criteria for defective/nondefective determination, solder shape defective/nondefective determining means 14 for performing the defective/nondefective determination according to the inspection standards and the three-dimensional shape data, and characteristic amount outputting means 16 for displaying or outputting the calculated data and displaying or outputting a solder shape causing "undertight" or "overtight" determination in setting a threshold.

The design information inputting means 4 inputs the design information required for generation of the three-dimensional solder shape data. The design information includes a component mounting position, component lead (electrode) height, land shape, solder wicking position, solder spreading position, and solder basic shape independent of design/manufacture conditions. The design information further includes the amount of solder to be printed as a criterion for defective/nondefective determination relating to a solder amount. The design information is input by operating a keyboard or the like to directly input data on a screen or by inputting data from a database.

In the prior art, the long-term data collection relating to a solder shape is required, because the characteristic amount relating to a solder shape whose frequency of occurrence is low is necessary to eliminate the "undertight" or "overtight" determination in the solder inspection. Accordingly, if the solder shape whose frequency of occurrence is low can be predicted to obtain the result of defective/nondefective determination and the characteristic amount of an inspection image, the requirement of long-term data collection can be eliminated and data adjustment can be made prior to achievement of manufacture performance.

In predicting a normal solder shape, it is necessary to calculate a surface tension or the like as considering design conditions such as wettability of a component and a solder amount and manufacture conditions such as a reflow oven temperature. However, in obtaining solder shapes whose frequency of occurrence is low, it is necessary to consider variations of various parameters in the calculation step, and it is very difficult to calculate all the solder shapes whose frequency of occurrence is low.

However, the surface of a solder shape is formed by smooth curves, and a basic solder shape is defined. Further, in adjusting the inspection data, it is only necessary to know changes in variation of a solder shape, and no accurate prediction of a solder shape is required. Accordingly, the solder shape calculating means 6 defines a basic solder shape and modifies the basic solder shape according to variations in component and land shapes, component mounting position, solder wicking amount, solder spreading amount, etc., thereby calculating a plurality of kinds of solder shapes.

More specifically, the solder shape calculating means 6 calculates hundreds of kinds of three-dimensional solder shape data to know the tendency of solder shapes in the case of considering manufacture variations. The manufacture variations include a deviation in mounting position, a difference in basic shape due to manufacture or solder material, and a solder wet condition. Of these manufacture variations, several to tens of kinds of variations are defined, and all the variations are combined to calculate hundreds of kinds of three-dimensional solder shape data.

Figure 3:
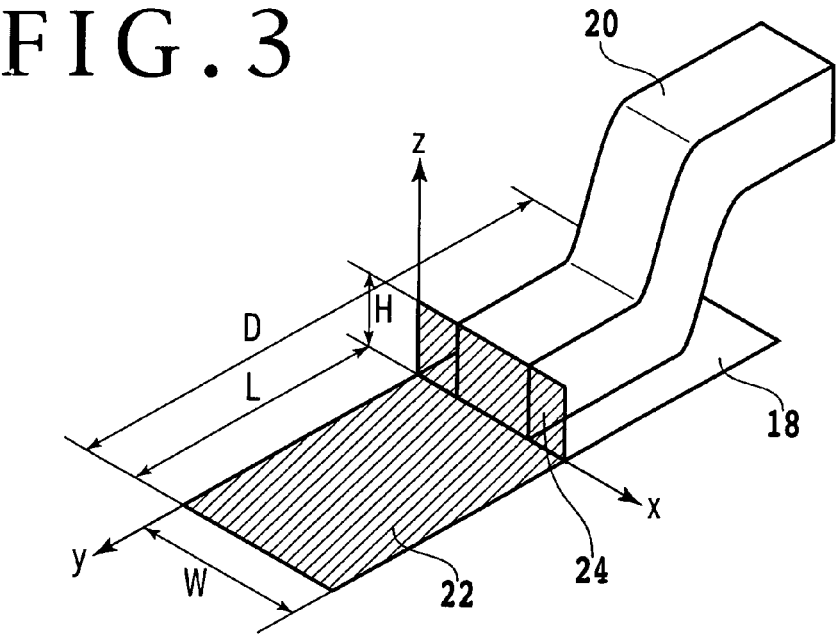
FIG. 3 is a perspective view showing the position of generation of three-dimensional solder shape data.

The position of generation of the three-dimensional solder shape data will now be described with reference to FIG. 3. The three-dimensional solder shape data to be calculated by a program are three-dimensional coordinate data representing the height (z axis) of a solder fillet to be formed within a land wetting plane 22 (x-y plane) extending from the front end of a land 18 to the front end of a lead 20.

Figure 2:
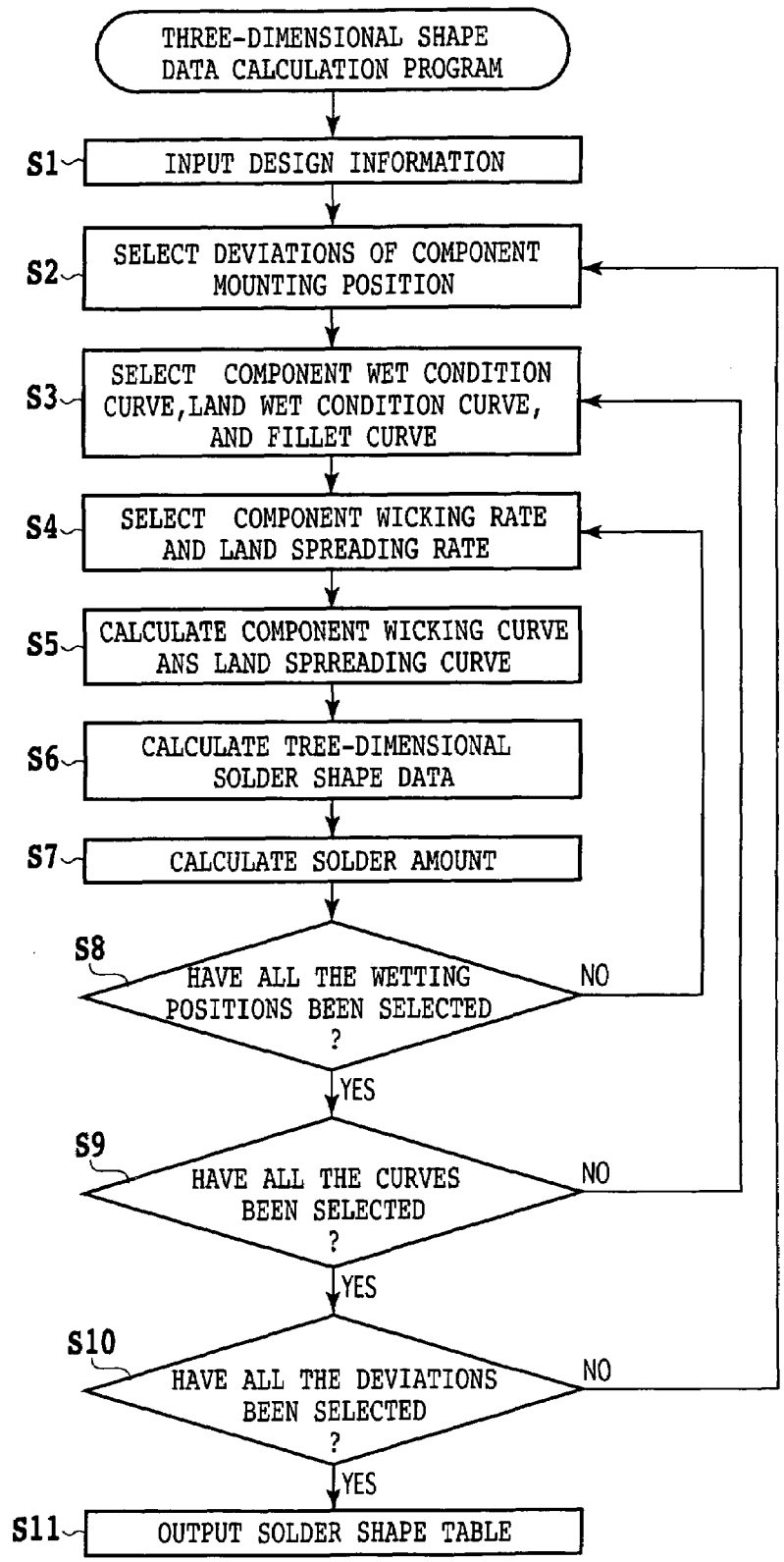
FIG. 2 is a flowchart showing the generation of a solder shape table.

The program for calculation of the three-dimensional solder shape data will now be described with reference to the flowchart shown in FIG. 2. In step S1, the design information including a component mounting position and a land shape is input. In step S2, a plurality of deviations of mounting position from a normal component mounting position obtained by the design information are calculated, and one of the deviations thus calculated is selected. In the case shown in FIG. 3, the lead 20 is mounted at a position spaced apart a distance L from the front end of the land 18 having a size of D×W.

Figure 4:
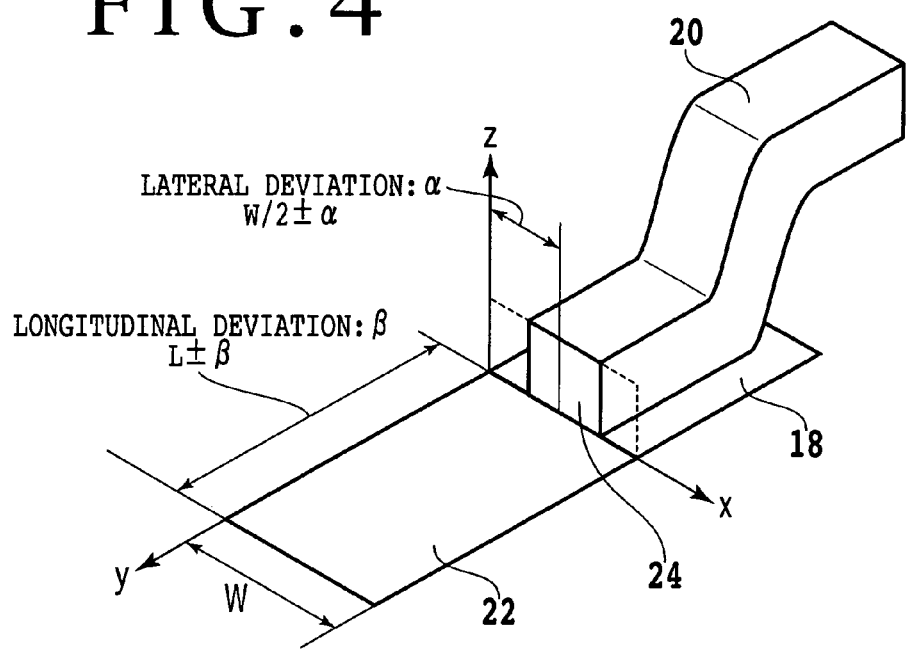
FIG. 4 is a perspective view for illustrating deviations in mounting position in relation to the three-dimensional solder shape data.

As shown in FIG. 4, a lateral deviation α from the center of the land 18 in its lateral direction and a longitudinal deviation β from the mounting position L are selected, wherein several kinds of deviations are selected in a non-defective range for the lateral deviation α and the longitudinal deviation β. Usually, a mounting position deviation is inspected in a mounting inspection (inspection for a component itself), and a deviation in solder shape may be considered only in a nondefective range. In step S3, different conditions of a solder bonded according to a difference in solder material as the design information input are expressed by using a basic pattern including three kinds of curves.

Figure 5A:
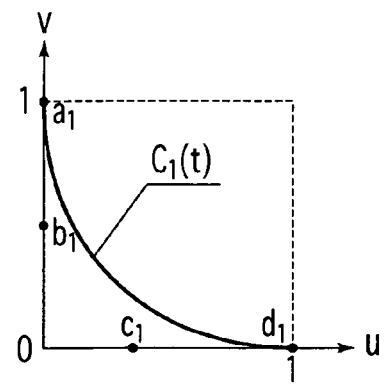
FIG. 5A is a graph showing a fillet curve.
Figure 5B:
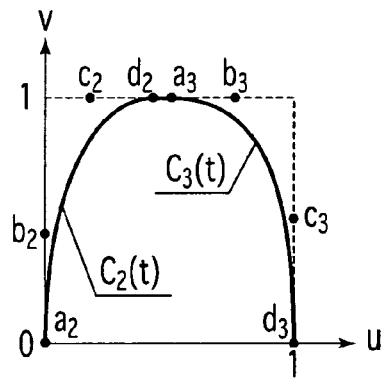
FIG. 5B is a graph showing a component wet condition curve.
Figure 5C:
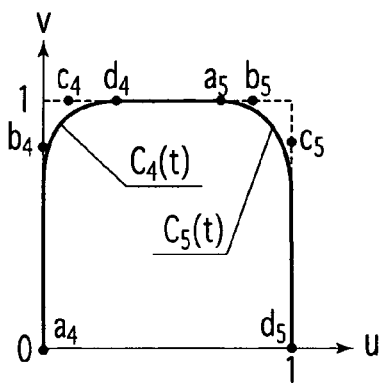
FIG. 5C is a graph showing a land wet condition curve.

This basic pattern is defined as the combination of three kinds of curves shown in FIGS. 5A to 5C. These three kinds of curves are a fillet curve shown in FIG. 5A for determining the solder shape from the front end of the lead 20 to the front end of the land 18, a component wet condition curve shown in FIG. 5B for representing a wet condition of the lead 20, and a land wet condition curve shown in FIG. 5C for representing a wet condition of the land 18. Each curve is defined as a four-point Bezier curve suitable for representation of a smooth shape of a solder fillet. This four-point Bezier curve is a curve $C_n(t)$ defined by four control points $a_n$, $b_n$, $c_n$, and $d_n$ shown below.

$$\vec{a}_n = a_{nu}\vec{u} + a_{nv}\vec{v},\ \vec{b}_n = b_{nu}\vec{u} + b_{nv}\vec{v},\ \vec{c}_n = c_{nu}\vec{u} + c_{nv}\vec{v},\ \vec{d}_n = d_{nu}\vec{u} + d_{nv}\vec{v}$$

$C_n(t)$ is defined as follows:

$$(1-t)^3 \vec{a}_n + 3t(1-t)^2 \vec{b}_n + 3t^2(1-t)\vec{c}_n + t^3 \vec{d}_n$$

Each basic pattern is expressed as follows:
For the fillet curve $F_1(u)$,
$F_1(u):C_1(t)$
For the component wet condition curve $F_2(u)$,
$F_2(u):C_2(t)\ \ldots\ (0 \leq u < d_{2u})$
$d_{2v}\ \ldots\ (d_{2u} \leq u \leq a_{3u})$
$C_3(t)\ \ldots\ (a_{3u} < u \leq 1)$
For the land wet condition curve $F_3(u)$,
$F_3(u):C_4(t)\ \ldots\ (0 \leq u < d_{4u})$
$d_{4v}\ \ldots\ (d_{4u} \leq u \leq a_{5u})$
$C_5(t)\ \ldots\ (a_{5u} < u \leq 1)$ Each of the component wet condition curve $F_2(u)$ and the land wet condition curve $F_3(u)$ is symmetrical in the horizontal axis. Further, each control point is set in the range of 0 to 1, because it is expanded or contracted according to a land shape, component shape, etc.

Figure 6A:
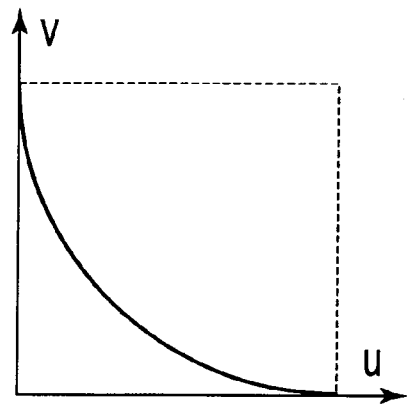
FIGS. 6A to 6C are graphs showing examples of the fillet curve.
Figure 6B:
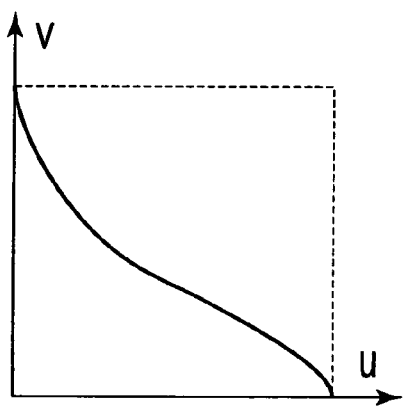
Figure 6C:
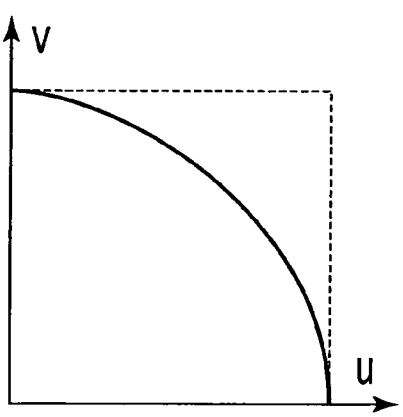
Figure 7A:
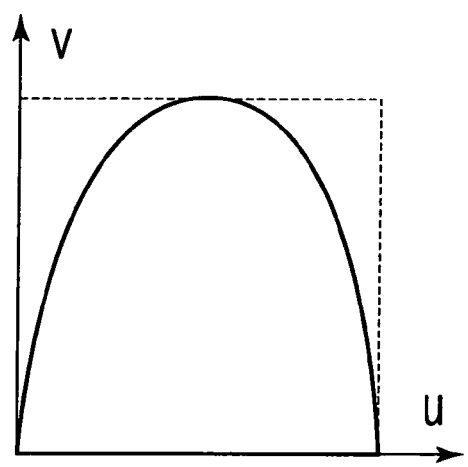
FIGS. 7A and 7B are graphs showing examples of the component wet condition curve.
Figure 7B:
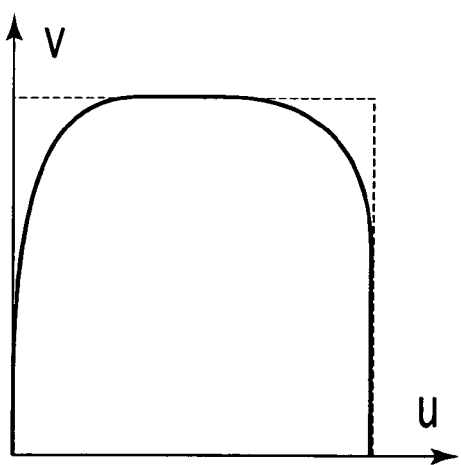

FIGS. 6A to 6C show examples of the fillet curve. This curve changes from FIG. 6A to FIG. 6C with changes in solder amount. FIGS. 7A and 7B show examples of the component wet condition curve. Although not shown, examples of the land wet condition curve are similar to those shown in FIGS. 7A and 7B. The program in this preferred embodiment uses tens of kinds of fillet curves, several kinds of component wet condition curves, and several kinds of land wet condition curves. In this case, a plurality of basic pattern data consisting of data on the three kinds of curves may be preliminarily stored in a solder shape pattern memory. Alternatively, the combination of the function expressing each curve and the control points for each curve may be preliminarily stored, and a plurality of basic pattern data may be generated by reading the stored contents. As another method, the control points and the function data may be input from the outside and a plurality of basic pattern data may be generated from these input parameters.

Referring back to FIG. 2, the program next proceeds to step S4 to select a component wicking rate p and a land spreading rate q. For example, a plurality of candidates of the component wicking rate p and the land spreading rate q are preliminarily stored, and the combination of these stored candidates is sequentially selected. The three-dimensional solder shape data are calculated from the component mounting position deviation, the solder basic pattern, and the solder wet condition mentioned above. This process of calculation will now be described.

Figure 8:
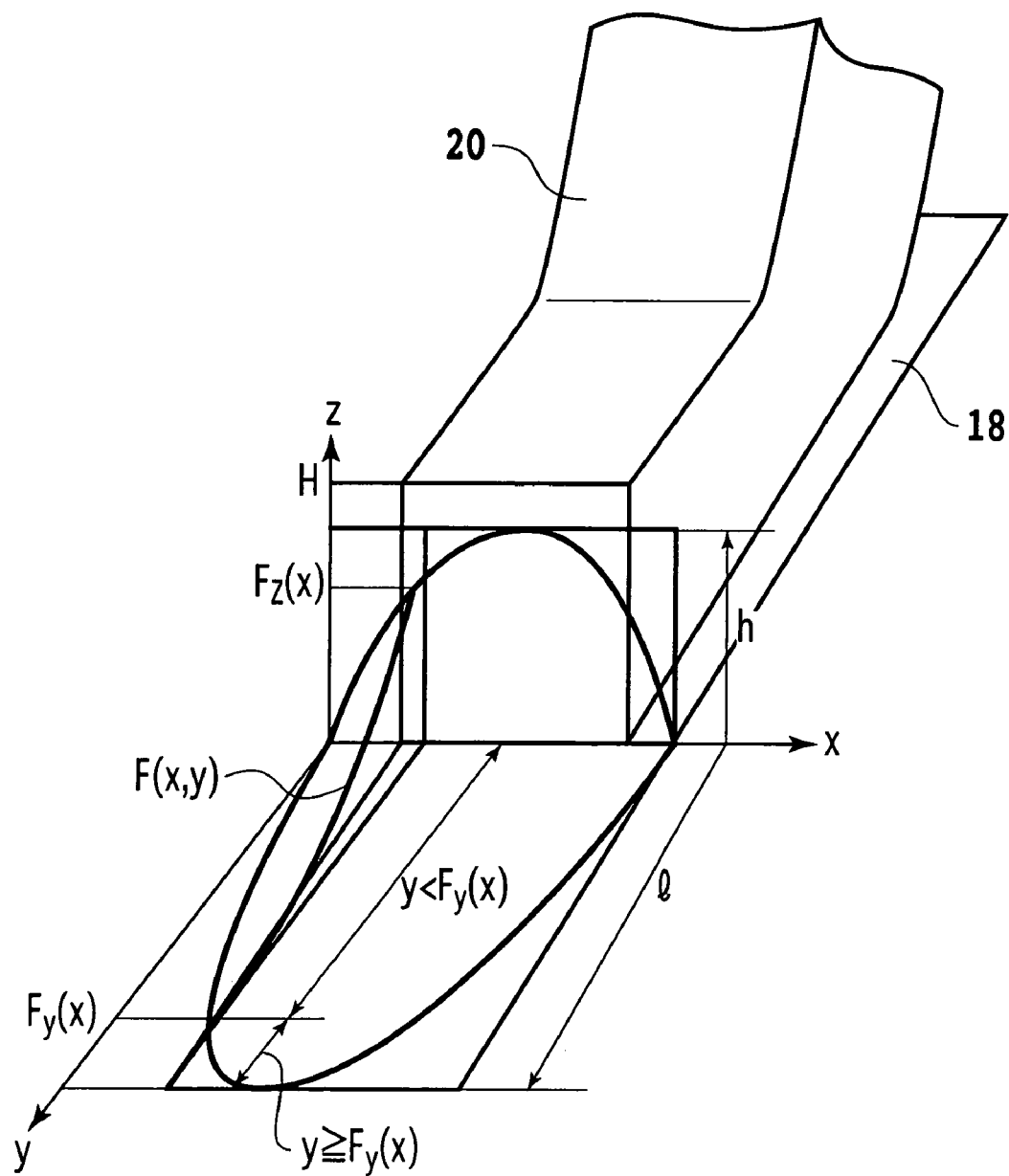
FIG. 8 is a perspective view for illustrating a calculation method for a three-dimensional solder shape model.

First, a solder wicking position h and a solder spreading position 1 are calculated (see FIG. 8).

$$h = pH$$

$$l = q(L+\beta)$$

where p and q are the solder wicking rate on the component and the solder spreading rate on the land, respectively, as selected above.

Next, a component wicking curve $F_2(x)$ is calculated from the component wet condition curve $F_2(u)$, the land width W, the lateral deviation a, and the solder wicking position h. That is, the component wicking curve $F_2(x)$ is obtained by expanding or contracting the component wet condition curve $F_2(u)$ in consideration of the lateral deviation a on the component wet condition plane represented by the land width W and the solder wicking position h.

$$F_z(x) = hF_2(x/2(W/2+\alpha))\ \cdots\ (0 \leq x \leq W/2+\alpha)$$

$$= hF_2((x-(W/2+\alpha))/2(W/2-\alpha)+1/2)\ \cdots\ (W/2+\alpha < x \leq W)$$

Next, a land spreading curve $F_y(x)$ is calculated according to the land wet condition curve $F_3(u)$, the land width W, and the solder spreading position 1. That is, the land spreading curve $F_y(x)$ is obtained by expanding or contracting the land wet condition curve $F_3(u)$ on the land wet condition plane represented by the land width W and the solder spreading position 1.

$$F_y(x) = lF_3(x/W)$$

However, in the case that the lateral deviation in component mounting has an influence on the land spreading curve, the calculation of the land spreading curve $F_y(x)$ is similar to that of the component wicking curve $F_z(x)$. The calculation of the component wicking curve $F_z(x)$ and the calculation of the land spreading curve $F_y(x)$ are performed in step S5 of the flowchart shown in FIG. 2.

Next, the program proceeds to step S6 to calculate three-dimensional solder shape data $F(x, y)$. The three-dimensional solder shape data (three-dimensional coordinate data) $F(x, y)$ is calculated by using the component wicking curve $F_z(x)$, the land spreading curve $F_y(x)$, and the fillet curve $F_1(u)$ as shown below.

$$F(x, y) = F_1(y/F_y(x))F_z(x)\ \cdots\ (y < F_y(x))$$

$$= 0\ \cdots\ (y \geq F_y(x))$$

The above equation represents three-dimensional data obtained by expanding or contracting the fillet curve $F_1(u)$ with the component wicking curve $F_z(x)$ set as a start point and the land spreading curve $F_y(x)$ set as an end point.

Figure 9A:
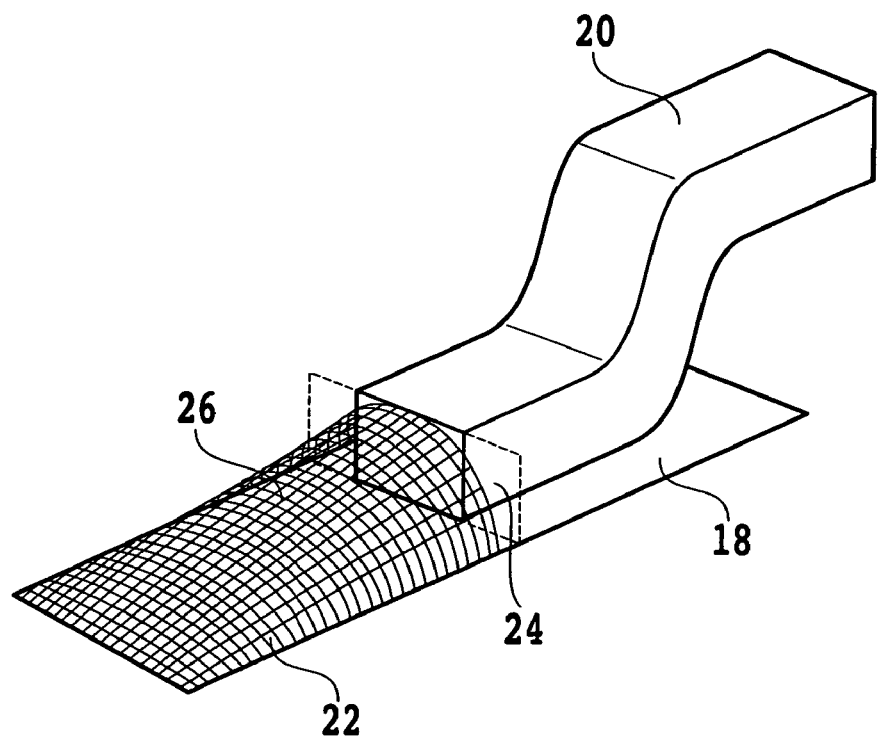
FIG. 9A is a perspective view showing an example of the solder shape model in the case of a lead component.
Figure 9B:
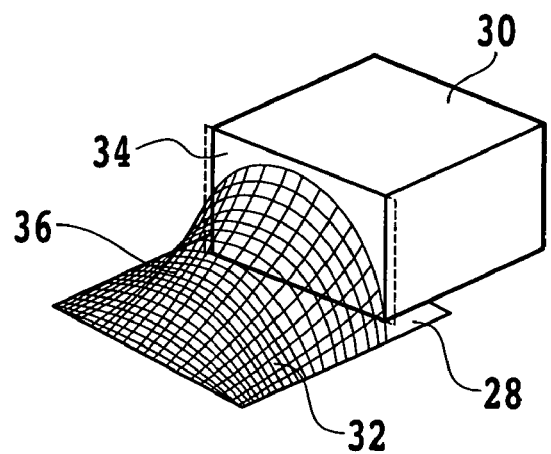
FIG. 9B is a perspective view showing an example of the solder shape model in the case of a chip component.

FIG. 9A shows a solder shape model in relation to a lead component 20. In FIG. 9A, reference numeral 26 denotes a three-dimensional solder shape obtained by calculation. FIG. 9B shows a solder shape model in relation to a chip component 30. In FIG. 9B, reference numerals 28, 30, 32, and 34 denote a land, chip component, land wet condition plane, and component wet condition plane, respectively. Further, reference numeral 36 denotes a three-dimensional solder shape obtained by calculation.

Next, the program proceeds to step S7 to calculate a solder amount V. The solder amount V is calculated from the following equation.

$$V = \iint F(x, y)dxdy$$

Next, it is determined whether or not all the wetting positions have been selected (step S8), whether or not all the curves have been selected (step S9), and whether or not all the deviations have been selected (step S10). In step S11, all the three-dimensional solder shapes for all the combinations of conditions are calculated and output as a solder shape table. Accordingly, the solder shape table is composed of a longitudinal deviation, lateral deviation, basic shape, component wicking rate, land spreading rate, solder amount, and three-dimensional shape data. The three-dimensional shape data and the solder amount are calculated from a component mounting position deviation (condition), solder basic pattern, and solder wet condition.

In summary, the solder shape calculating means 6 calculates a plurality of solder shape data from a component mounting position, solder wicking position, solder spreading position, etc. input. The solder shape calculating means 6 further uses a fillet curve showing a contour in a longitudinal section of a solder central portion, a wicking curve showing a solder wicking condition on a component surface, and a spreading curve showing a solder spreading condition on a land surface, thereby calculating three-dimensional coordinate data from the fillet curve with the wicking curve set as a start point and the spreading curve set as an end point.

Figure 11:
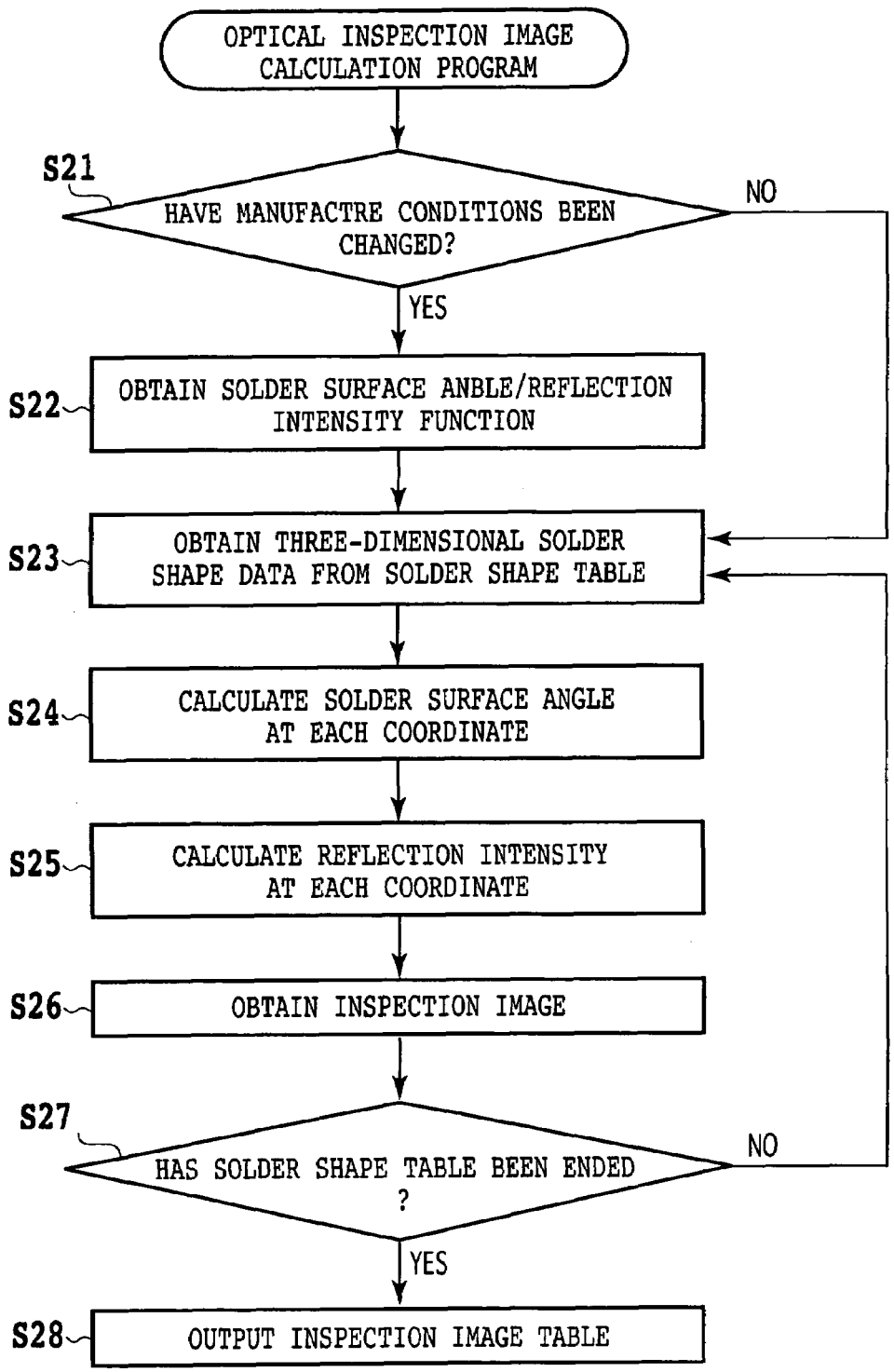
FIG. 11 is a flowchart showing the generation of an inspection image by the optical inspection method.
Figure 12:
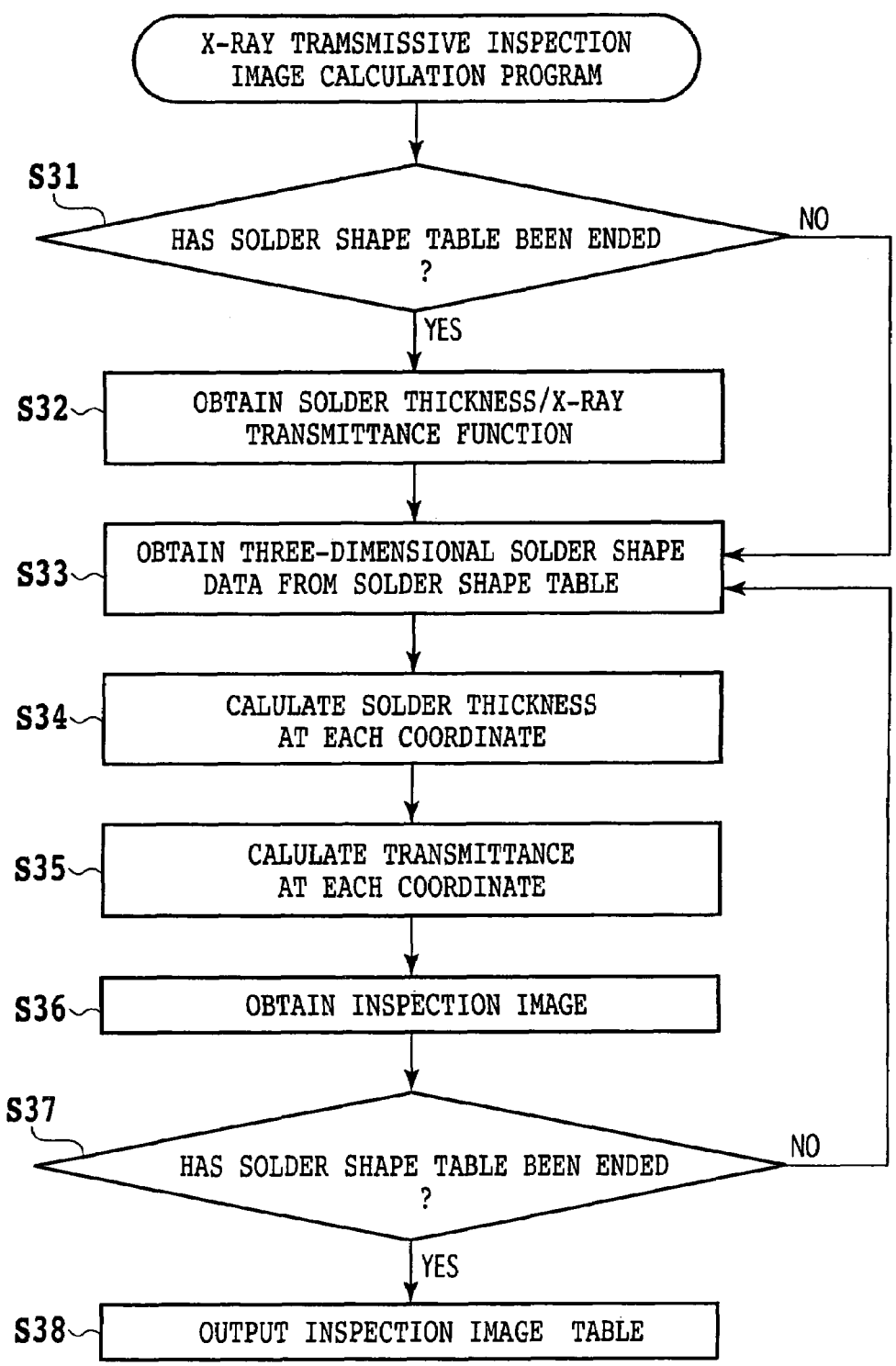
FIG. 12 is a flowchart showing the generation of an inspection image by the X-ray transmissive inspection method.

Referring again to FIG. 1, the inspection image calculating means 8 selects an inspection method by an appearance inspecting machine and calculates an inspection image by using the three-dimensional shape data in the solder shape table. The inspection method means either the optical inspection method or the X-ray transmissive inspection method. FIG. 11 is a flowchart of inspection image generation according to the optical inspection method, and FIG. 12 is a flowchart of inspection image generation according to the X-ray transmissive inspection method. In the case of the optical inspection method shown in FIG. 11, it is first determined whether or not the manufacture conditions have been changed in step S21. If the answer in step S21 is yes, the program proceeds to step S22 to obtain a solder surface angle and a reflection intensity function, whereas if the answer in step S21 is no, the program jumps to step S23 to obtain the three-dimensional solder shape data from the solder shape table shown in FIG. 10.

On the other hand, in the case of the X-ray transmissive inspection method, it is determined whether or not the solder shape table has been ended in step S31 of the flowchart shown in FIG. 12. If the answer in step S31 is yes, the program proceeds to step S32 to obtain a solder thickness and an X-ray transmittance function, whereas if the answer in step S31 is no, the program proceeds to step S33 to obtain the three-dimensional solder shape data from the solder shape table shown in FIG. 10. In other words, an inspection image obtaining function providing a detected intensity is used in each inspection method. In the case of the optical inspection method, the inspection image obtaining function is a function of the angle of a solder surface and the detected intensity of reflected light, and in the case of the X-ray transmissive inspection method, the inspection image obtaining function is a function of the thickness of a solder bonded and the detected intensity of transmitted X rays. A method of calculating the detected intensity by actual measurement will now be described.

The inspection image obtaining function is a function of the parameter such as the angle of a solder surface (in the optical inspection method) or the thickness of a solder bonded (in the X-ray transmissive inspection method) and the detected intensity as mentioned above. Accordingly, the solder shape must be specified to obtain the function. However, it is difficult to measure the shape of a solder fillet formed between a normal component and a land, and the present invention therefore uses a dome-shaped solder fillet formed on a land at an unmounted portion.

Figure 13:
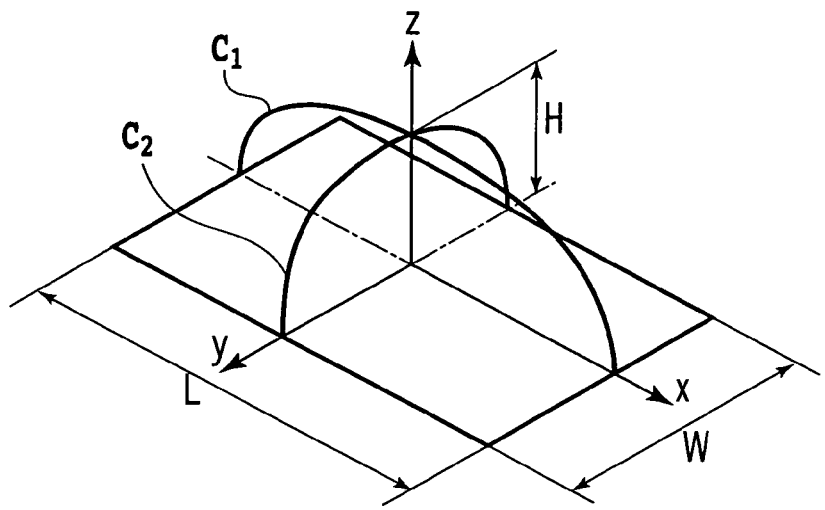
FIG. 13 is a perspective view showing the shape of an unmounted portion.

In the case that the solder fillet is formed like a dome, the model therefor may be defined by the curves shown in FIG. 13. In FIG. 13, $C_1$ and $C_2$ show elliptical curves.

The height of the fillet is expressed as follows:

$$C_1: z = H\sqrt{1 - 4x^2/W^2}$$

$$C_2: z = H\sqrt{1 - 4y^2/L^2}$$

The angle of the fillet is expressed as follows:

$$C_1: \theta = \tan^{-1}\left(\frac{4Hx}{\sqrt{W^2 - 4x^2}}\right)$$

$$C_2: \theta = \tan^{-1}\left(\frac{4Hy}{\sqrt{L^2 - 4y^2}}\right)$$

The intensity distribution of an inspection image along the axis can be obtained from the inspection image of the solder fillet. The inspection image obtaining function in the optical inspection method can be obtained from the angle of the fillet and the intensity distribution along the axis, and the inspection image obtaining function in the X-ray transmissive inspection method can be obtained from the height of the fillet and the intensity distribution along the axis.

Figure 14:
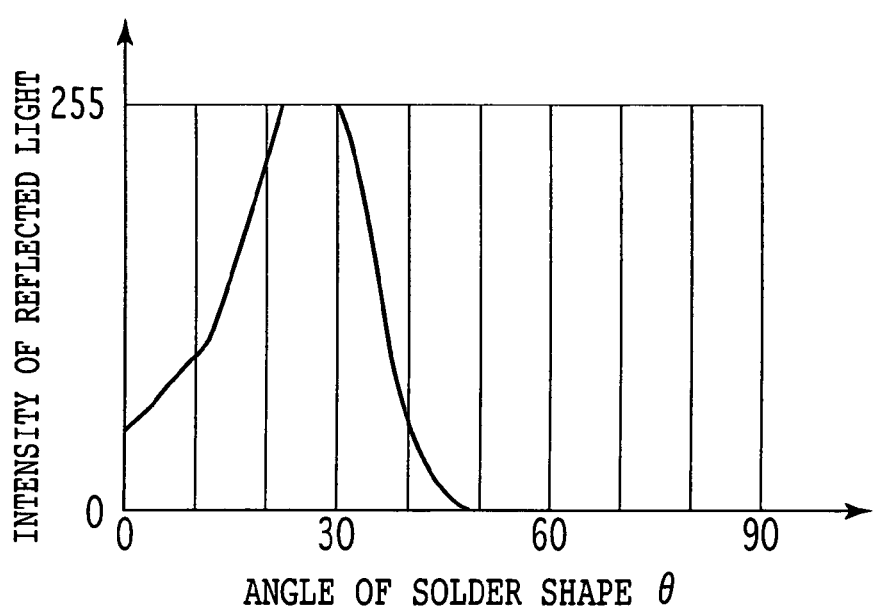
FIG. 14 is a graph showing an example of an inspection image obtaining function by the optical inspection method.

FIG. 14 shows an example of the inspection image obtaining function in the optical inspection method. In FIG. 14, the horizontal axis represents the surface angle of a solder fillet, and the vertical axis represents the intensity of reflected light. In this example, the intensity of reflected light is maximum at an angle of 20° to 30° for the solder surface angle. The inspection image obtaining function is expressed by fitting to a theoretical equation or two-dimensional coordinate data. The inspection image is calculated for each solder shape in the solder shape table shown in FIG. 10 as obtained by the solder shape calculating means 6 by using the above inspection image obtaining function.

Figure 15:
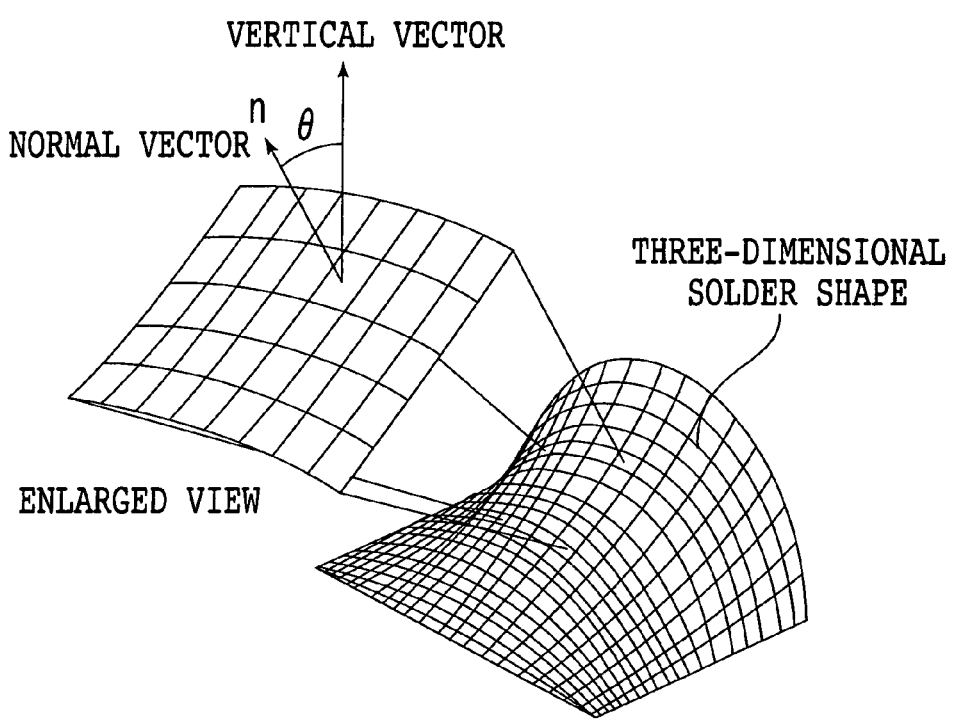
FIG. 15 is a perspective view for illustrating a generation method for an optical inspection image.

In the case of obtaining an optical inspection image, a normal vector to a solder fillet surface at each coordinate is calculated as shown in FIG. 15 from the three-dimensional solder shape data to calculate the angle θ formed between the normal vector and a vertical vector (step S24). Next, the intensity of reflected light at each coordinate is calculated in step S25 to thereby obtain an inspection image from the angle θ of the solder shape and the intensity of the reflected light (step S26). In the case of obtaining an X-ray transmissive inspection image, the thickness h of the solder fillet at each coordinate is calculated from the three-dimensional solder shape data in step S34 shown in FIG. 12. Next, the transmittance of X rays at each coordinate is calculated in step S35 to thereby obtain an inspection image from the thickness h of the solder shape and the transmittance of the X rays in step S36.

In the case of the optical inspection method shown in FIG. 11, it is next determined whether or not the solder shape table has been ended in step S27. If the answer in step S27 is yes, the program proceeds to step S28 to output an inspection image table, whereas if the answer in step S27 is no, the steps S23 to S26 are repeated. In the case of the X-ray transmissive inspection method shown in FIG. 12, it is then determined whether or not the solder shape table has been ended in step S37. If the answer in step S37 is yes, the program proceeds to step S38 to output an inspection image table, whereas if the answer in step S37 is no, the steps S33 to S36 are repeated.

Figure 16A:
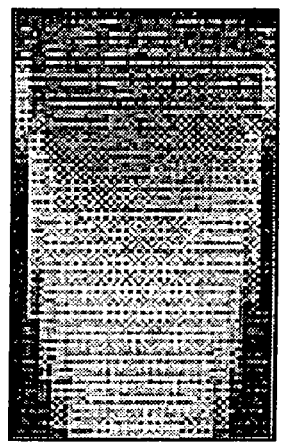
FIG. 16A is an example of the optical inspection image in relation to the lead component shown in FIG. 9A.
Figure 16B:
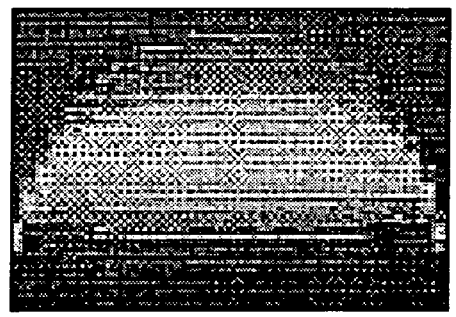
FIG. 16B is an example of the optical inspection image in relation to the chip component shown in FIG. 9B.
Figure 17A:
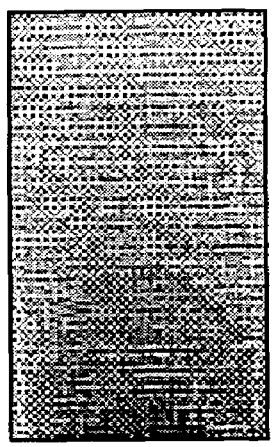
FIG. 17A is an example of the X-ray transmissive inspection image in relation to the lead component shown in FIG. 9A.
Figure 17B:
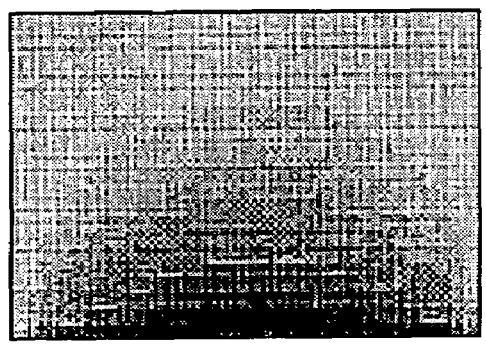
FIG. 17B is an example of the X-ray transmissive inspection image in relation to the chip component shown in FIG. 9B.

FIGS. 16A and 16B show examples of the optical inspection image obtained by using the inspection image calculation program for the solder shape model on the lead component shown in FIG. 9A and the solder shape model on the chip component shown in FIG. 9B, respectively. FIGS. 17A and 17B show examples of the X-ray transmissive inspection image respectively corresponding to FIGS. 16A and 16B. That is, FIGS. 16A and 17A show inspection images on the lead component shown in FIG. 9A, and FIGS. 16B and 17B show inspection images on the chip component shown in FIG. 9B.

In summary, the inspection image calculating means 8 has inspection image obtaining means for obtaining an inspection image by using an inspection image obtaining function showing the intensity of the inspection image with respect to the solder characteristic amount such as the angle or thickness of a solder fillet. The inspection image obtaining function is calculated by using an actual inspection image of a solder fillet formed on a land at an unmounted portion as a function showing the intensity of the inspection image with respect to the solder characteristic amount such as the angle or thickness of the solder fillet.

Figure 18:
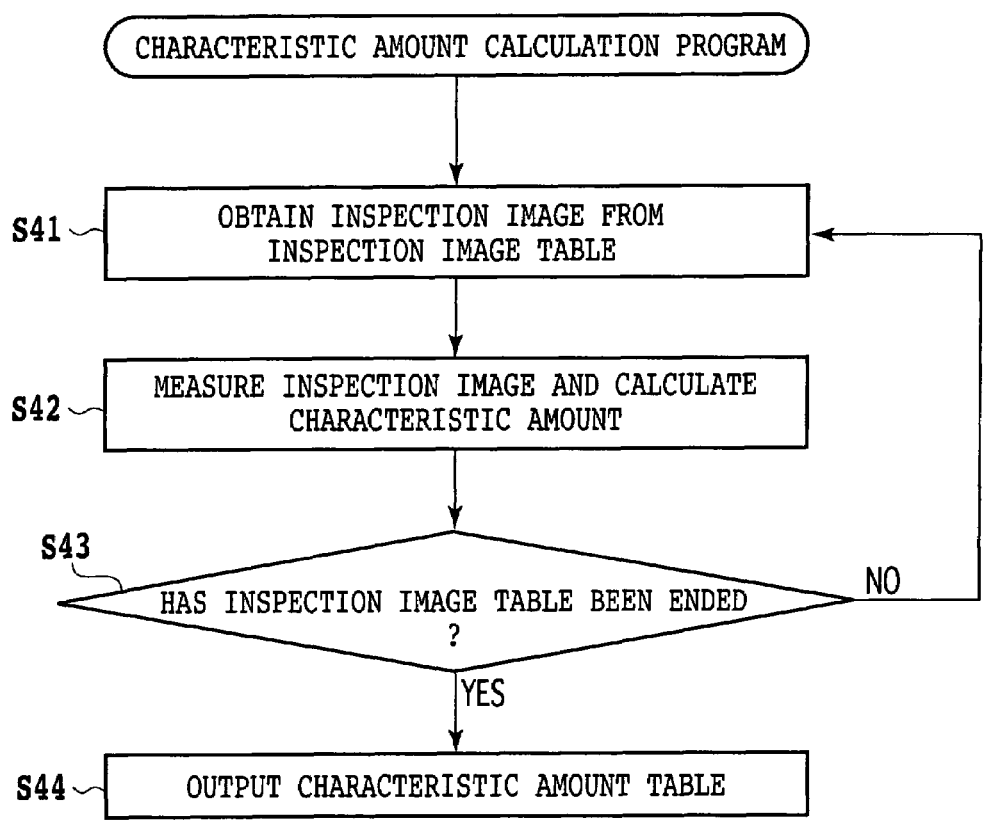
FIG. 18 is a flowchart showing the generation of a characteristic amount.

Referring again to FIG. 1, the characteristic amount calculating means 10 calculates a characteristic amount from the inspection image obtained by the inspection image calculating means 8 according to the measuring method by the optical or X-ray transmissive appearance inspecting machine, thereby generating a characteristic amount table. FIG. 18 is a flowchart showing a characteristic amount calculation program. In step S41, an inspection image is obtained from the inspection image table. In step S42, the inspection image is measured to calculate a characteristic amount. In step S43, it is determined whether or not the inspection image table has been ended. If the answer in step S43 is yes, the program proceeds to step S44 to output a characteristic amount table shown in FIG. 20, whereas if the answer in step S43 is no, the steps S41 and S42 are repeated. The characteristic amount table is a table obtained by adding a characteristic amount to the inspection image table.

Referring again to FIG. 1, the inspection standard inputting means 12 is means for inputting inspection standards relating to a solder amount and solder wettability. As the inspection standard on the solder amount, an upper limit (threshold to an excess solder amount) and a lower limit (threshold to a short solder amount) for the amount of the solder formed at the front end of the land are input by the inspection standard inputting means 12. The upper limit and the lower limit are proportions or absolute values for the solder amount input by the design information inputting means 4. However, it should be noted that a solder fillet is formed near the rear end of the land in the case of a lead component, so that the amount of the solder formed at the front end of the land is smaller than the solder amount input by the design information inputting means 4.

The inspection standard on the solder amount can also be determined from a solder shape. Accordingly, the inspection standard may be set for the fillet curve of the solder basic pattern. As the inspection standard on the solder wettability, lower limits for the solder wicking rate and the solder spreading rate are input by the inputting means 12. These wicking rate and spreading rate are inspection standards for those used in the solder shape table generation program shown in FIG. 2.

While a reference value or criterion for classifying the solder shape into a nondefective and a defective is usually set, the defective may be subclassified into several kinds (the degree of defective may be defined). For example, the solder shape may be classified into three kinds, i.e., a complete defective, a near-good defective, and a nondefective. By defining such a degree of defective, it is possible to know the degree of any defective subjected to "undertight" determination in the circumstances where a small amount of "undertight" determination may be caused in order to reduce a large amount of "overtight" determination. In other words, it is possible to realize optimum data setting considering all the detection rate of defective, the overtight determination, and the undertight determination.

Figure 19:
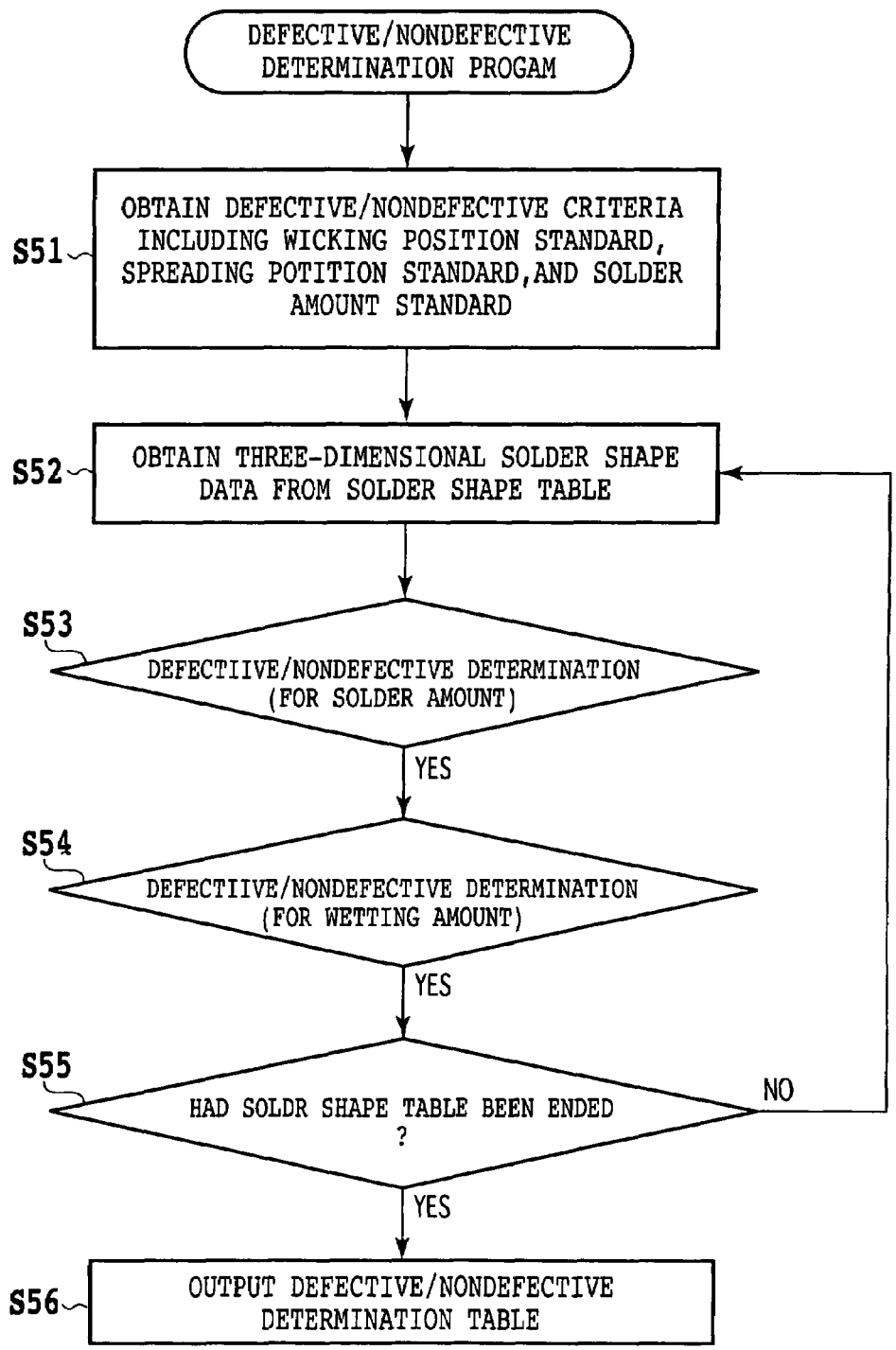
FIG. 19 is a flowchart showing the defective/nondefective determination for a solder shape.

Referring again to FIG. 1, the solder shape defective/ nondefective determining means 14 determines whether each solder shape generated by the solder shape calculating means is defective or nondefective by using the inspection standards input by the inspection standard inputting means 12. FIG. 19 is a flowchart for the defective/nondefective determination. In step S51, the wicking position standard, the spreading position standard, and the solder amount standard are obtained. In step S52, the three-dimensional solder shape data is obtained from the solder shape table.

In step S53, the solder amount or basic shape pattern is compared with the inspection standard on the solder amount to perform the defective/nondefective determination on the solder amount. In step S54, the wicking rate or spreading rate is compared with the inspection standard on the wetting amount to perform the defective/nondefective determination on the wetting amount. In step S55, it is determined whether or not the above determination has been ended for all the data in the solder shape table shown in FIG. 10. If the answer in step S55 is no, the steps S52 to S54 are repeated.

If the answer in step S55 is yes, the program proceeds to step S56 to output a defective/nondefective determination table shown in FIG. 20. In the case that the degree of defective is defined, the number indicating the degree of defective is output. That is, the solder shape defective/ nondefective determining means 14 performs the defective/ nondefective determination for a virtual solder shape by using the inspection standard specifying a defective range on the solder amount or solder wetting amount. Preferably, the solder shape defective/nondefective determining means 14 classifies a defective into a plurality of ranks according to the degree of defective.

Referring again to FIG. 1, the characteristic amount outputting means 16 is means for outputting the solder shape table shown in FIG. 10 and the inspection image table, the characteristic amount table, and the defective/nondefective determination table shown in FIG. 20. By setting a threshold for each measured value in the characteristic amount table, the inspection data can be adjusted as checking the solder shape to be determined as "undertight" or "overtight". The threshold for each measured value as obtained above is input into the optical or X-ray transmissive appearance inspecting machine, thereby allowing an improvement in accuracy of soldering inspection performed by the appearance inspecting machine.

According to the present invention as described above, a plurality of solder shape data providing changes in solder shape due to deviations in component mounting position and variations in solder wettability and solder amount can be obtained according to information given in designing. Further, an inspection image, defective/nondefective determination result, and characteristic amount accompanied by the above solder shape data can also be obtained. Accordingly, as compared with the prior art wherein the long-term collection of characteristic amounts or inspection images is required for the adjustment of inspection data, the characteristic amount for the adjustment of inspection data can be quickly obtained according to the present invention.

Further, as compared with the prior art wherein the defective/nondefective determination by the worker is ambiguous, causing the ambiguity of inspection data adjustment, the present invention can achieve a precise defective/ nondefective determination according to the inspection standards. Further, variations in inspection image due to any factors such as a solder surface condition other than a solder shape are neglected according to the present invention, thereby obtaining a characteristic amount neglecting an extremely rare inspection image.

The present invention can also exhibit the following additional effects. First, by defining the degree of defective and classifying it into a plurality of ranks, it is possible to concentrate a defective rank intended to be detected upon data adjustment and thereby to control the defective detection rate, overtight determination, and undertight determination. Secondly, data adjustment can be performed as checking a solder shape determined as undertight or overtight. Thirdly, even when manufacture conditions or the like such as a solder material are changed, a characteristic amount for readjusting data can be easily obtained only by changing the inspection image obtaining function.

The present invention is not limited to the details of the above described preferred embodiments. The scope of the invention is defined by the appended claims and all changes and modifications as fall within the equivalence of the scope of the claims are therefore to be embraced by the invention.

What is claimed is:

1. A characteristic amount calculating device for soldering inspection, comprising:
   design information inputting means for inputting design information of an inspection object;
   inspection standard inputting means for inputting an inspection standard specifying a defective range on solder amount or solder wetting amount;
   solder shape calculating means for calculating shape information of a plurality of virtual solder fillets based on said design information;
   inspection image calculating means for calculating an inspection image according to said shape information of said virtual solder fillets;
   characteristic amount calculating means for calculating characteristic amounts of virtual solder shapes from said inspection images;
   solder shape defective/nondefective determining means for determining whether the virtual solder shapes are defective or nondefective from said shape information of said virtual solder fillets by using said inspection standard; and
   characteristic amount outputting means for outputting said characteristic amounts of said virtual solder shapes and a result of defective/nondefective determination to compare said characteristic amounts with said result of defective/nondefective determination to thereby determine a threshold value of said characteristic amount.

2. A characteristic amount calculating device according to claim 1, wherein said design information includes a component shape and a land shape, and said solder shape calculating means calculates a plurality of solder shape data according to said component shape and said land shape input.

3. A characteristic amount calculating device according to claim 1, wherein said design information includes a component mounting position, a solder wicking position, a solder spreading position, and a solder basic shape independent of design/manufacture conditions; and
   said solder shape calculating means calculates a plurality of solder shape data according to said component mounting position, said solder wicking position, said solder spreading position, and said solder basic shape input.

4. A characteristic amount calculating device according to claim 1, wherein said solder shape calculating means calculates three-dimensional coordinate data by using a fillet curve showing the contour of said solder fillet, a wicking curve showing a solder wicking condition on a component surface, and a spreading curve showing a solder spreading condition on a land surface.

5. A characteristic amount calculating device according to claim 1, wherein said inspection image calculating means has inspection image obtaining means for obtaining said inspection image by using an inspection image obtaining function indicating the intensity of said inspection image with respect to the characteristic amount including the angle or thickness of said solder fillet.

6. A characteristic amount calculating device according to claim 5, wherein said inspection image obtaining function is calculated by using an actual inspection image of a solder fillet formed on a land at an unmounted portion as a function showing the intensity of said inspection image with respect to the characteristic amount including the angle or thickness of said solder fillet.

7. A characteristic amount calculating device according to claim 1, wherein said inspection standard includes a solder amount standard, a solder wicking standard, and a solder spreading standard.

8. A characteristic amount calculating device according to claim 7, wherein said solder shape defective/nondefective determining means performs the defective/nondefective determination for a virtual solder shape by using said inspection standard specifying a defective range on a solder amount or a solder wetting amount.

9. A characteristic amount calculating device according to claim 1, wherein said solder shape defective/nondefective determining means classifies the defective solder shape into a plurality of ranks according to the degree of defective.

10. A characteristic amount calculating device according to claim 1, wherein said characteristic amount outputting means outputs information selected from the group consisting of a solder shape, solder amount, wetting amount, and inspection image shown by three-dimensional coordinate data, in addition to said characteristic amount and said defective/nondefective determination result.

11. A characteristic amount calculating device according to claim 1, wherein said characteristic amount outputting means specifies a threshold related to said characteristic amount to thereby display a solder shape determined as undertight or overtight.

12. A characteristic amount calculating method for soldering inspection, comprising:
   inputting design information of an inspection of object;
   inputting an inspection standard specifying a defective range on solder amount or solder wetting amount;
   calculating shape information of a virtual solder fillet based on said design information;
   calculating an inspection image according to said shape information of said virtual solder fillet;
   calculating a characteristic amount of virtual solder shape from said inspection image;
   determining whether the virtual solder shape is defective or nondefective from said shape information of said virtual solder fillet by using said inspection standard; and
   outputting the characteristic amount of said virtual solder shape and a result of defective/nondefective determination to compare said characteristic amount with said result of defective/nondefective determination to thereby determine a threshold value of said characteristic amount.

* * * * *